US009014812B2

(12) United States Patent
Filippello

(10) Patent No.: US 9,014,812 B2
(45) Date of Patent: Apr. 21, 2015

(54) METHOD FOR PREVENTION OF PRESBYOPIA AND GLAUCOMA, AND MEANS FOR CARRYING OUT SAID TREATMENT

(75) Inventor: Massimo Filippello, Catania (IT)

(73) Assignee: Sooft Italia SpA, Montegiorgio (Ascoli Piceno) (IT)

( * ) Notice: Subject to any disclaimer, the term of this patent is extended or adjusted under 35 U.S.C. 154(b) by 384 days.

(21) Appl. No.: 12/997,003

(22) PCT Filed: Jun. 11, 2009

(86) PCT No.: PCT/IT2009/000255
§ 371 (c)(1),
(2), (4) Date: Dec. 9, 2010

(87) PCT Pub. No.: WO2009/150688
PCT Pub. Date: Dec. 17, 2009

(65) Prior Publication Data
US 2011/0082518 A1   Apr. 7, 2011

(30) Foreign Application Priority Data

Jun. 12, 2008  (IT) .............................. RM2008A0309

(51) Int. Cl.
*A61N 1/36* (2006.01)
*A61N 1/04* (2006.01)
*A61N 1/05* (2006.01)
(52) U.S. Cl.
CPC .......... *A61N 1/36046* (2013.01); *A61N 1/0452* (2013.01); *A61N 1/0456* (2013.01); *A61N 1/0472* (2013.01); *A61N 1/05* (2013.01)
(58) Field of Classification Search
USPC ........................................... 607/53; 606/4, 5
See application file for complete search history.

(56) References Cited

U.S. PATENT DOCUMENTS

| 4,603,697 A * | 8/1986 | Kamerling ...................... 607/53 |
| 5,782,894 A | 7/1998 | Israel |
| 6,083,251 A | 7/2000 | Shindo |
| 2006/0271025 A1 * | 11/2006 | Jones et al. ....................... 606/4 |

FOREIGN PATENT DOCUMENTS

JP          11-57030 A       3/1999

OTHER PUBLICATIONS

International Search Report, dated Mar. 2, 2010, from corresponding PCT application. A.P. Nesterov et al., "Effect of ciliary muscle electrical stimulation on ocular hydrodynamics and visual function in patients with glaucoma", Vestnik Oftamologii—Annals of Ophthalmology, Medicina, Jul. 1, 1997, pp. 12-14, vol. 113, No. 4; English-language Abstract; Cited in International Search Report.

* cited by examiner

*Primary Examiner* — Christopher D Koharski
*Assistant Examiner* — Michael D Abreu
(74) *Attorney, Agent, or Firm* — Young & Thompson

(57) ABSTRACT

A method of for prevention of presbyopia and glaucoma envisages stimulation of the ciliary body to determine contraction thereof via a low-voltage d.c. current sent in the form of pulse trains. This contraction, if applied in a rhythmic way at a constant frequency, subjects the ciliary muscle to a passive gymnastics increasing the force of contraction thereof, the dimensions, and the efficiency. This increase of force enables the crystalline to be moved with greater efficiency and consequently increases the power of accommodation thereof. The contraction of the ciliary muscle stretches the tendinous formation in direct contact with the sclero-corneal trabeculate and increases the distance between the lamellae of the sclero-corneal angle, restoring the natural function of the trabeculate and thus preventing glaucoma. Stimulation of the anatomical area corresponding to the ciliary body occurs through the use of conductive electrodes positioned in direct contact with the bulbar conjunctiva at an appropriate distance from the corneal limbus.

16 Claims, 2 Drawing Sheets

METHOD FOR PREVENTION OF PRESBYOPIA AND GLAUCOMA, AND MEANS FOR CARRYING OUT SAID TREATMENT

FIELD OF THE INVENTION

The present invention describes an innovative method for prevention of presbyopia and/or onset of glaucoma, and the means for implementation thereof.

The method envisages electrostimulation, for a suitable time of chronaxy of the ciliary body by means of appropriate current pulse trains through electrodes set in contact with the conjunctiva at 2 to 5 mm from the corneal limbus in order for the sclero-corneal trabeculate to be kept efficient.

This is obtained, according to a preferred embodiment, via a scleral contact lens containing at least two pairs of electrodes that are to come into contact with the conjunctiva in an area at a distance of between 3 and 5 mm from the corneal limbus, at the anatomical site of the ciliary body.

Further characteristics and advantages of the invention will emerge clearly from the ensuing detailed description with reference to the annexed plates of drawings, which illustrate a preferred embodiment thereof merely by way of non-limiting example. In the plates of drawings.

REMARKS ON THE ANATOMY AND PHYSIOPATHOLOGY OF THE CILIARY BODY

Figure 1:
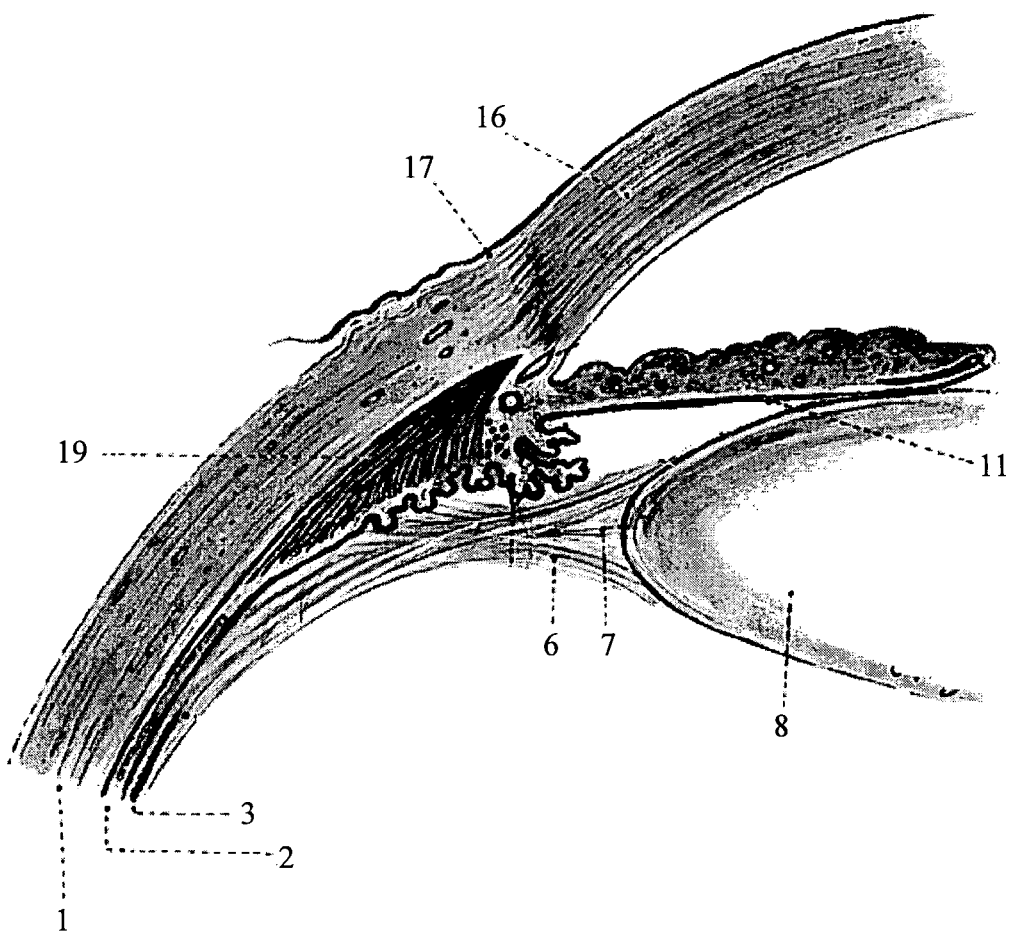
FIG. 1 is a cross-sectional view of the ciliary body with the iris and the crystalline.

The ciliary body is a concentric ring adherent to the deep face of the sclera and prominent within the anterior segment towards the median axis of the eye; it is the intermediate portion of the vascular coat and, in the context of the uvea (vascular coat of the eye), is set between the choroid behind and the iris 11 forwards. In cross section, as may be seen in FIG. 1, the ciliary body, designated by 19, has the shape of a triangle with an external long side, in contact with the sclera 1, of which it coats the deep face as a prosecution of the choroid 2, with an internal median side, coated by the outer leaflet of the retina 3, which faces the inside of the eye and with a short side facing forwards and divided into two portions by the radix 9 of the iris. The first portion is the ciliary ring (orbiculus ciliaris) or pars plana, the second portion is the pars plicata. The structure is connected to the crystalline 8 through the zonule 7, a dense mesh of filaments (zonular fibres 6) that attach to the outer rim of the crystalline. The short side of the ciliary body 19 is responsible for the secretion of the aqueous humour. Contained within the ciliary body 19 is the ciliary muscle. The muscle is in direct contact with the ocular structure responsible for outflow of the aqueous humour (sclero-corneal trabeculate).

The ciliary muscle occupies the antero-external part of the ciliary body. As has been said, from the three-dimensional standpoint it has a prismatic-triangular shape. A small tendon connects the muscle to the sclero-corneal trabeculate. The muscle is formed by the meridional fibres (Bruecke's muscle) and by circular fibres (Mueller's muscle). The meridional fibres are connected through the tendon with the trabecular system. The entire muscular structure is connected to the crystalline through the zonular fibres. Consequently, the contraction-decontraction enables the crystalline to be moved and in practice activates the mechanism of accommodation. This fundamental process for focusing close objects close up is obtained with a modification of the curvature of the crystalline. The outermost area of the crystalline, the capsule, is quite elastic, a quality that keeps it always under tension and causes the lens to assume a more or less spherical configuration.

When the ciliary muscle is relaxed, the ciliary processes keep contracted the suspensory ligaments of the Zinn's zonule, which, in turn, pull on the capsule of the crystalline at the equatorial height, and this causes a reduction of the curvature of the faces of the crystalline, which thus becomes less convex, enabling vision of distant objects.

When, instead, the ciliary muscle contracts, the suspensory ligaments relax; consequently, the capsule is pushed outwards and both faces of the crystalline become more convex, thus enabling the vision of close objects.

Remarks on Physiopathology of Presbyopia

If the ciliary muscle contracts, the crystalline stretched by the zonular fibres flattens its shape; instead, if the muscle distends, the crystalline becomes globe-shaped. The modification of the shape of the crystalline serves for focusing objects close up. The maximum contraction of the crystalline corresponds to the minimum focal distance; instead, the maximum decontraction enables focusing at infinity.

The degree of accommodation is given by the interval between the minimum reading distance and the maximum reading distance. This interval is called power of accommodation and is measured in diopters. The most accredited theories that explain the mechanism of accommodation have been postulated by Helmholtz and Schachar. According to both of these theories, the function of the ciliary muscle is fundamental for maintaining the mechanism of accommodation active. With ageing, this muscle undergoes a progressive reduction of efficiency and this, together with the reduction of the elasticity of the crystalline, explains presbyopia.

Figure 2:
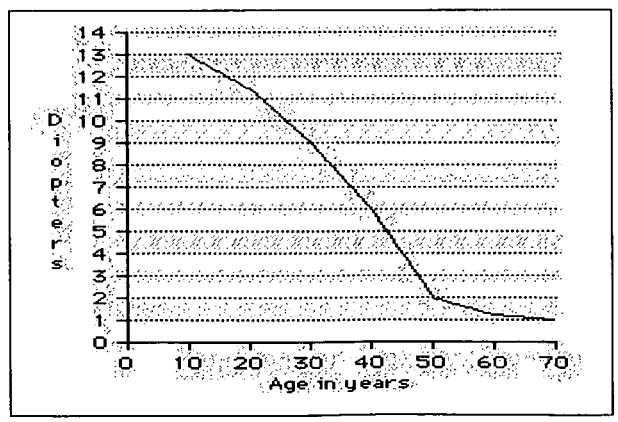
FIG. 2 is a graph that illustrates the reduction of the power of accommodation as a function of ageing.

As may be seen in FIG. 2, ageing determines a progressive reduction of the power of accommodation.

The graph highlights that at the age of approximately thirteen the amplitude is 13 diopters, whereas over sixty it drops to less than 1 diopter. The diopter is a unit of measurement that is equal to the reciprocal of the focul distance expressed in meters. For instance, 3 diopters correspond to a distance of 33 cm (1/30=0.33). In this case, 3 diopters are required for focusing at 33 cm. It is evident that at the age of sixty focusing undergoes a sharp drop, and the eye is practically no longer able to focus objects located at a distance of less than one meter.

The theories that seek to explain the progressive deterioration of accommodation presuppose that over the years the crystalline becomes progressively less elastic, and consequently it is necessary to have a ciliary muscle that is increasingly efficient to obtain a good power of accommodation.

Physiopathology of Glaucoma

The glaucomatous desease has numerous causes that lead to different types of glaucoma. In this patent application, reference will be made to the most common and frequent forms of glaucoma referred to as open-angle glaucoma.

The eye maintains its internal pressure constant thanks to a complex system of circulation of liquids. In particular, the aqueous humour is a liquid that fills the anterior and posterior chambers of the eye. It is produced by an anatomical structure called ciliary body, which in general does not undergo any reduction in efficiency over time. Instead, the system of drainage represents the role for which an anatomical structure called sclero-corneal trabeculate is responsible. This is formed by a dense mesh of fibres, which between them constitute a reticulum, which in turn filters the aqueous humour towards the ocular lymphatic and venous systems. In time, around forty years of age, and precisely simultaneously with onset of presbyopia, there may occur a progressive restriction of the trabecular meshes. Consequently, the system of drainage of the aqueous humour undergoes a slow and progressive loss of efficiency determining an increase in the ocular pressure and ultimately the glaucomatous desease. The trabecular meshes are kept efficient through the contraction of the ciliary muscle, which, being connected via a tendinous connection to the trabeculate, keeps it efficient thanks to the action of continuous stretching of the trabecular meshes. The latter are to be envisioned as an infinite series of microholes, which, only if they are kept pervious, are able to allow easy passage the aqueous humour. Precisely around forty years of age, in concomitance with onset of presbyopia, there occurs the greater statistical onset of open-angle glaucoma. In both cases, there is the loss of force of contraction of the ciliary muscle, which favours onset of glaucoma and presbyopia.

The U.S. Pat. No. 5,782,894 relates a device and method that satisfies the need of restoring the loss of near vision resulting from presbyopia without the use of eyeglasses. The device and the method focus the eyes upon a near object by electrically stimulating the ciliary muscles when the eyes converge to view the near object. Preferably, the ciliary muscles are stimulated proportionally to the contraction of the internal rectus muscles to ensure that the eyes focus to the specific distance of the near object. In said document, a sensor is surgically installed on the internal rectus muscle of each eye; a stimulator is surgically installed on the ciliary muscle of each eye; and a control unit which communicates between the sensors and stimulators is surgically installed under the skin.

Electrical stimulation of the extraocular muscles (ocular recti) of the eye has been proposed to treat strabismus in U.S. Pat. No. 4,271,841 titled "Electro-ocular Stimulation System" issued Jun. 9, 1981 to Harry G. Friedman. This patent discloses a body implantable unit including an electrode implanted over or in the extraocular muscle. The electrode is coupled by a lead to a portion of the implantable unit which develops the stimulation signal. The purpose of the stimulation signal is to trigger contraction of the agonistic extraocular muscle.

While, repeated, controlled electrical stimulations of the ciliary muscle to increase aqueous outflow through the trabecular meshwork and reduce intraocular pressure and thereby prevent or treat open angle glaucoma are the object of the invention described in U.S. Pat. No. 4,603,697. The described stimulations allow the lens of the eye to widen and focus on near objects and thereby prevent or treat presbyopia.

The U.S. Pat. No. 6,083,251 discloses a treatment apparatus including a low-frequency signal generator for generating low-frequency signals of 20 Hz which have a gradually increasing amplitude and are effective to stimulate the ciliary muscle as well.

Studies on the effect of ciliary muscle electrical stimulation on ocular hydrodynamics and visual function in patients with glaucoma have been performed by Nesterov et al., and described in the document published in 1997 in Vestnik Oftalmologii-Annals of Ophtahalmologi, Medicina, Moscow 113: 12-14. To perform the electrostimulation Nesterov et al. have been employed a device comprising means for generating trains of rectangular bipolar pulses, e.g. compensated biphasic square-wave pulses, wherein the width of each pulse is between 1-15 ms and the intensity of current is in a range of 0.5-10 μA, and means for stimulating of the ciliary body comprising four electrodes positioned on a lens that can be positioned in direct contact with the area of the ciliary muscle during stimulation. However, according to results of Nesterov, intraocular pression has decreased only in 6% of patients affected by glaucoma following one cycle of electrostimulation and in 16% after six months of treatment.

So, despite the amplitude of experience in the technical field there still need of improved therapeutic protocols for the treatment of ocular diseases characterized by the loss of force of contraction of the ciliary muscle.

DESCRIPTION OF THE INVENTION

Following upon the clinical tests conducted, the inventor has found that stimulation of the ciliary body using two or more electrodes with appropriate current pulse trains determines contraction of the muscle. This contraction, if applied in a rhythmic way at a constant frequency, is able to subject the ciliary muscle to a passive gymnastics, increasing the force of contraction and dimensions and efficiency of the muscle. This increase of force enables the crystalline to move with a greater efficiency and consequently increase its power of accommodation. Likewise, the contraction of the ciliary muscle stretches the tendinous formation in direct contact with the sclero-corneal trabeculate and enables, through stretching thereof, an increase in the distance between the lamellae of the sclero-corneal angle. The action of stretching on the trabecular meshes favours de-obstruction thereof and facilitates the outflow of the aqueous humour.

Stimulation of the anatomical area corresponding to the ciliary body occurs through the use of conductive electrodes positioned in direct contact with the bulbar conjunctiva at a distance of 2 to 5 mm from the corneal limbus. The corneal limbus is the area of passage between the cornea and the sclera. The electrodes must be in direct contact with the area of the ciliary muscle for the entire time of stimulation.

A preferred embodiment of the present invention substantially envisages a device comprising:

means for generating a train of square-wave pulses or compensated biphasic square-wave pulses, wherein the width of each pulse ranges from 50 to 250 μs;

means for stimulation of the ciliary body, which comprise two or more conductive electrodes that can be positioned in direct contact with the area of the ciliary muscle for the entire time of stimulation, and means for performing the stimulation of one or more desired quadrant of the four quadrants in which it is possible dividing the ciliary body, with different sequences and with different timing in order to differentiate the stimulation effects and to improve the therapeutic efficacy.

According to a peculiar characteristic of the invention, to facilitate the contact of the electrodes in both eyes and facilitate the work of the operator as well as treatment, the electrodes are mounted on a scleral contact lens.

Figure 3:
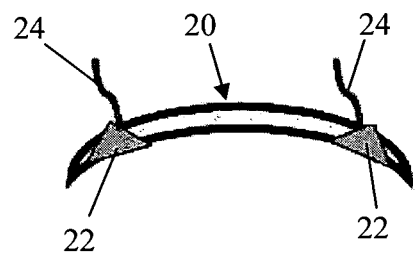
FIG. 3 is a schematic illustration, in profile, of a scleral contact lens according to the invention, containing two pairs of electrodes from which the electrical wire that connects up to the electrostimulator exits.

A preferred embodiment of said lens is illustrated, merely by way of example, in FIG. 3, which is a profile view of a contact lens 20 containing four electrodes 22, from which there exits the electrical wire 24 that connects up to the electrostimulator (not illustrated).

Figure 4:
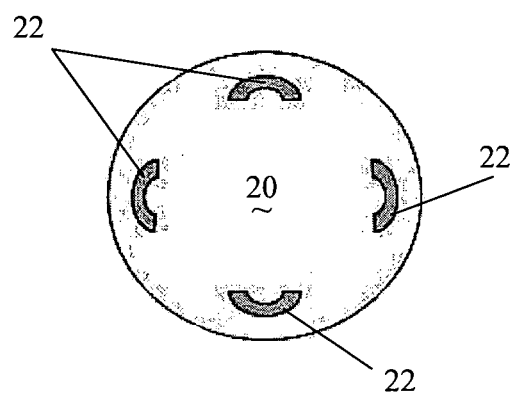
FIG. 4 shows the positioning of the electrodes on the rear face of the lens that is to come into direct contact with the bulbar conjunctiva.

FIG. 4 is a plan view from beneath of the same lens 20, which highlights the position of the four electrodes 22 on the face of the lens that comes into direct contact with the bulbar conjunctiva.

The total diameter of the lens ranges from 16 to 20 mm (basic radius from 7.0 to 9.5 mm). The electrodes are positioned at an equal distance apart. The distance between each electrode and the centre of the contact lens ranges from 8 to 11 mm. The distance between the electrode and the outer rim of the lens ranges from 1 to 4 mm.

The different positioning of the electrodes and the diameter of the lens, which ranges from 16 to 20 mm, arises from the need to adapt the lens to the different dimensions of the human eye.

The electrodes must have an ample contact on the conjunctiva: their ideal shape must consequently be like the one illustrated in FIG. 4, i.e., arched, or alternatively rectangular with chamfered edges or else simply spherical. The minimum dimensions are 2 mm in width and 1 mm in height for the non-spherical shapes and 2 mm for the spherical shape.

It has been found that stimulation of the ciliary structure is to be carried out in different ways and with different times in order to be able to differentiate the effects. In other words, the effect of stimulation of the ciliary body with d.c. microcurrents is dose- and time-dependent.

Consequently, the sequence of stimulation is extremely important to obtain the desired result.

According to the present invention, three sequences of stimulation are envisaged:
1) parallel sequence;
2) crossed sequence; and
3) rotary sequence;
as illustrated hereinafter.

1) Parallel sequence: this envisages opposed vertical and horizontal contractions. The muscle is stimulated by hemispheres. This sequence determines revascularization and tonification of the ciliary muscle. The contraction obtained determines the maximum tension on the tendon of the sclero-corneal trabeculate and consequently exerts the maximum action on the sclero-corneal trabeculate.

2) Crossed sequence: this sequence occurs by causing the muscle to contract according to opposed quadrants in alternate phases.

3) Rotary sequence: sequential stimulation with contractions divided according to quadrants. The four quadrants into which the muscle is divided are stimulated one after another according to a rotary scheme.

In the prevention of presbyopia, the succession of a crossed sequence and a rotary sequence is advantageously used, which determines an increase in the muscular mass and in the force of contraction, but does not produce significant effects on the sclero-corneal trabeculate.

The current used for prevention of presbyopia is a low-voltage d.c. current of a square wave type, preferably compensated biphasic square-wave, which is sent to the ciliary body in the form of pulse trains.

The times of chronaxy (in neuro-electrophysiology, minimum time of duration of a current, of known, very small, intensity necessary for stimulation of a nerve to achieve a useful effect, i.e., contraction of the muscle) range from 50 to 250 µs, preferably 200 µs, and correspond substantially to the width of each pulse.

The frequency of repetition of the pulse train is comprised between 1 and 200 Hz, preferably 12 Hz.

The peak current intensity is comprised between 11 and 100 mA, preferably 11-13 mA.

For prevention of glaucoma a low-voltage d.c. current of a square-wave type or compensated biphasic square wave is used, which is sent to the ciliary body in the form of pulse trains.

In the clinical testes better results have been obtained by square-wave type having time of chronaxy ranging from 50 to 250 µs, preferably 200 µs. The frequency of repetition of the pulse train is comprised between 1 and 200 Hz, the current has a peak intensity comprised between 11 and 100 mA, preferably 11-13 mA.

The low frequencies function principally for stimulation of the muscle, whereas the high frequencies have a revascularizing and tonifying predominance, with increase of the oxygenation of the muscular fibre. The time and frequency of stimulation enable the different results to be obtained as specified hereinafter.

Prevention of Glaucoma

When the ciliary muscle loses efficiency there occurs a reduction in the contraction, and the tendon that connects the muscle to the trabeculate exerts an progressively weaker tensile action on the trabecular meshes responsible for natural drainage of the aqueous humour. A reduction in efficiency of the trabeculate consequently determines an increase of the ocular pressure and subsequently an irreversible damage to the optical nerve and to the retinal nerve fibres. Currently, there exist different both medical and surgical therapies able to reduce the ocular pressure, but, instead, there does not exist any treatment that is able to restore the natural functioning of the trabeculate and consequently exert a function of prevention of glaucoma.

To obtain a greater efficiency of the sclero-corneal trabeculate it is sufficient to carry out stimulation for a few minutes in so far as the purpose is to stretch and widen the meshes of the sclero-corneal trabeculate through stretching of the tendon that connects the ciliary muscle to the trabeculate itself.

Stimulation of the muscle is to be performed at the anatomical site of the muscle situated at approximately 3.5 mm from the corneal limbus. To obtain stimulation of the entire muscle the electrodes are to be applied in an opposed way, at 3 and 9 o'clock or else at 12 and 6 o'clock (parallel stimulation). Stimulation aimed at prevention of glaucoma is to be performed only in the eye concerned for a duration of 5 to 15 min and is to be repeated every 7 days for at least 4 times. The d.c. current is supplied with a frequency comprised between 1 and 200 Hz according to the waveform used and the desired result. The higher the frequency used, the greater the effect on the trabeculate. The peak currents must not be higher than 100 mA. During treatment, the patient must remain with the electrodes in contact with the conjunctiva, endeavouring to prevent eye movements. To facilitate treatment, a scleral contact lens of the diameter of 16-20 mm has been developed, to which two electrodes have been applied in opposition and only in the proximity of the edge. Said electrodes are in direct contact with the conjunctiva at an average distance of 3.5 mm from the limbus. The contact lenses, of dimensions ranging from 16 to 20 mm, have been studied to enable contact of the electrodes on corneas of variable diameter. Stimulation through the contact lens enables the eyelids to be kept closed, from the fissure of which there exit only the wires of the electrodes. The latter are connected to a dedicated electrostimulator that is able to supply d.c. current.

During stimulation, there is also noted a rhythmic contraction of the pupillary muscles with consequent rhythmic meiosis and mydriasis. These movements induced by the d.c. current are the proof that the treatment has the right efficacy and power. During stimulation, the patient may note also a slight formication of the eyelids and in general of the entire eye.

Prevention of Presbyopia

The reduction of force of the ciliary muscle, which starts at around forty years of age seems to be linked to a progressive loss of elasticity of the crystalline. This important lens of the eye has the capacity of contracting and consequently varying of its own curvature to be able to focus objects close up. After forty years of age, with the progressive reduction of the elasticity of the lens, the ciliary muscle is forced to contract with greater force. The need for a vigorous contraction is not, however, sufficient to counter ageing of the crystalline and gradually the ciliary muscle undergoes a progressive atrophy.

The simultaneous stimulation of the two ciliary muscles is to be performed for 10 min with current having a frequency comprised between 1 and 200 Hz and maximum peak intensity of 100 mA. The treatment is to be repeated every 3 to 5 days for at least 1 month. During treatment, must be prevented simultaneous stimulation of the pupillary muscles, visible through the rhythmic contraction of the pupillary foramen. Stimulation of the muscle is able to restore tone to the ciliary muscle, which consequently starts to contract with greater vigour and is able to move the crystalline in a more efficient way. The stimulation site is located at 3.5 mm from the corneal limbus and in this case a four-point stimulation in opposition is necessary (3, 6, 9, 12 o'clock) to restore muscular tone. Stimulation is to be performed with crossed sequence for the first 5 min and with rotary sequence for the following 10 min, for a total of 15 min for each sitting. To obtain a real prevention of presbyopia through the maintenance of the muscular tone of the ciliary muscle, stimulation must always be simultaneous in both eyes. Stimulation is to be performed on alternate days for the first week and subsequently every 7 days for the next 8 weeks. The treatment is painless except for a slight formication that may be experienced in the entire ocular bulb.

A preferred embodiment of the invention has been described herein. It is on the other hand evident that numerous modifications and variations can be made thereto by persons skilled in the branch, without departing from the sphere of protection of the present industrial patent right, as defined by the ensuing claims.

LIST OF REFERENCES INDICATED IN THE FIGURES

| | |
|---|---|
| 1: sclera | 2: choroid |
| 3: retina | 6: zonular fibres |
| 7: zonule | 8: crystalline |
| 11: iris | 16: cornea |
| 17: corneal limbus | 19: ciliary muscle |
| 20: contact lens | 22: electrodes |
| 24: electrical wire. | |

However, the invention and the field of protection sued for is better described by means of the following claims.

The invention claimed is:

1. A method for preventing presbyopia and/or onset of glaucoma, comprising the steps of:
performing electrostimulation of the ciliary body by applying different sequences of pulse trains of low-voltage d.c. current on one or more of the four quadrants of ciliary body, the electrostimulation of the ciliary body occurring through conductive electrodes positioned in direct contact with the bulbar conjunctiva at a distance of 2 to 5 mm from corneal limbus; and
differentiating effects of said electrostimulation on the ciliary body,
wherein during said performing step, said pulse trains are in form of square-wave or compensated biphasic square-wave,
wherein a time of chronaxy of the electrostimulation of the ciliary body ranges from 50 to 250 µs, and the peak current intensity is between 11 and 100 mA.

2. The method according to claim 1, wherein the electrostimulation of the ciliary body occurs through at least two pairs of electrodes with a crossed sequence of stimulation so as to cause contraction of opposed quadrants of the four quadrants into which the ciliary muscle is divided in alternate phases.

3. The method according to claim 2, wherein the electrostimulation of the ciliary body occurs through at least two pairs of electrodes with rotating stimulation causing contraction of the four quadrants into which the ciliary muscle is divided one after another according to a rotary scheme.

4. The method according to claim 3, further comprising, after said electrostimulation step, performing a stimulation with crossed sequence followed by a stimulation with rotary sequence, and determining an increase of the muscular mass and of the force of contraction, without giving rise to significant effects on the sclero-corneal trabeculate.

5. The method according to claim 1, wherein the electrostimulation is obtained via a scleral contact lens containing electrodes coming into direct contact with the bulbar conjunctiva in an area at the distance of between 2 and 5 mm from the corneal limbus.

6. The method according to claim 5, wherein the electrodes are positioned at an equal distance apart, a distance between each electrode and the center of the contact lens ranges from 8 to 11 mm.

7. The method according to claim 6, wherein, a distance between each electrode and an outer rim of the lens ranges from 1 to 4 mm.

8. The method according to claim 1, comprising:
providing a scleral contact lens containing at least two pairs of electrodes, the electrodes being positioned at an equal distance apart, the distance between each electrode and the center of the contact lens being in a range of from 8 to 11 mm, and the distance between each electrode and the outer rim of the lens being in a range of from 1 to 4 mm;
applying the contact lens to an eye of the subject, wherein the at least two pairs of electrodes are in direct contact with the bulbar conjunctiva, the contact lens being configured to position the electrodes in an area at the distance of between 2 and 5 mm from the corneal limbus; and
performing said electrostimulation.

9. The method according to claim 8, wherein the contact lens has a diameter of from 16 to 20 mm.

10. The method according to claim 1, wherein the electrostimulation of the ciliary body occurs through at least one pair of electrodes with a parallel sequence of stimulation of the ciliary muscle to give rise to vertical and/or horizontal opposed contractions and said determining steps include determining a maximum tension on the tendon of the sclero-corneal trabeculate.

11. The method according to claim 1, wherein a time of chronaxy of the electrostimulation of the ciliary body is 200 µs, and the peak current intensity is between 11-13 mA.

12. The method according to claim 1, wherein, for the treatment of glaucoma, the electrostimulation of the ciliary body occurs only in an eye concerned for a duration of 5 to 15 minutes and is repeated every 7 days for at least 4 times.

13. The method according to claim 1, wherein, for the treatment of presbyopia, the electrostimulation of the ciliary body occurs as a crossed sequence for the first 5 min of a 15 minute treatment setting, followed by a rotary sequence for the following 10 min, for a total of 15 minutes for each treatment setting, and such stimulation is performed on alternate days for a first week and subsequently every 7 days for a following 8 weeks, the stimulation always being performed in both eyes.

14. The method according to claim 1, wherein the electrostimulation is obtained via a scleral contact lens containing at least two pairs of electrodes coming into external direct contact with the bulbar conjunctiva in an area at the distance of between 2 and 5 mm from the corneal limbus, at the anatomical site of the ciliary body, the electrodes being positioned at an equal distance apart, a distance between each electrode and a center of the contact lens ranges from 8 to 11 mm, and a distance between each electrode and an outer rim of the lens ranges from 1 to 4 mm.

15. The method according to claim 1, wherein the electrostimulation is obtained via a scleral contact lens containing at least two pairs of electrodes coming into external direct contact with the bulbar conjunctiva.

16. The method according to claim 1, wherein the electrostimulation is obtained via a scleral contact lens containing at least two pairs of electrodes coming into external direct contact with the bulbar conjunctiva in an area at the distance from the corneal limbus.

* * * * *